United States Patent
De La Peña Mireles et al.

(10) Patent No.: US 11,649,194 B2
(45) Date of Patent: May 16, 2023

(54) **BACTERIAL INOCULATING FORMULATION BASED ON A MICROORGANISM CONSORTIUM OF GENUS *CALOTHRIX* SP. TO INCREASE YIELD AND QUALITY OF VEGETABLE CROPS, THE METHOD FOR MANUFACTURING THE FORMULATION AND USES THEREOF**

(71) Applicant: NEWPEK S.A. DE C.V., San Pedro Garza García (MX)

(72) Inventors: Iván Alejandro De La Peña Mireles, Monterrey (MX); Miguel Angel Bautista Ramírez, General Escobedo (MX); Salvador Ocegueda Estrada, Celaya (MX); Héctor Álan Barrón León, Irapuato (MX)

(73) Assignee: Newpek S.A. DE C.V., San Pedro Garza García (MX)

( * ) Notice: Subject to any disclaimer, the term of this patent is extended or adjusted under 35 U.S.C. 154(b) by 434 days.

(21) Appl. No.: 16/024,961

(22) Filed: Jul. 2, 2018

(65) Prior Publication Data
US 2019/0008161 A1   Jan. 10, 2019

(30) Foreign Application Priority Data
Jul. 4, 2017   (MX) .................. MX/a/2017/008876

(51) Int. Cl.
| | |
|---|---|
| *C05F 11/08* | (2006.01) |
| *A01N 63/20* | (2020.01) |
| *C12N 1/12* | (2006.01) |
| *C12N 11/02* | (2006.01) |

(52) U.S. Cl.
CPC .............. *C05F 11/08* (2013.01); *A01N 63/20* (2020.01); *C12N 1/12* (2013.01); *C12N 11/02* (2013.01)

(58) Field of Classification Search
CPC ........... C12N 1/12; C12N 11/02; C05F 11/08; A01N 63/20
See application file for complete search history.

(56) References Cited

U.S. PATENT DOCUMENTS

| | | | | |
|---|---|---|---|---|
| 5,501,720 | A * | 3/1996 | Buchholz ............ | C05C 9/02 71/28 |
| 6,251,826 | B1 * | 6/2001 | Kulik ................. | C05F 11/00 504/117 |
| 2010/0300166 | A1 * | 12/2010 | Mena Campos .... | A01N 63/00 71/6 |
| 2011/0036009 | A1 * | 2/2011 | Bissonnette ........ | C05G 5/23 71/33 |
| 2014/0345341 | A1 * | 11/2014 | Fiato ................. | C05B 17/00 71/7 |
| 2014/0352376 | A1 * | 12/2014 | Carpenter .......... | C05G 5/30 71/6 |

FOREIGN PATENT DOCUMENTS

| | | | |
|---|---|---|---|
| KR | 20040028034 A | * 4/2004 | |
| WO | WO-2016167668 A2 | * 10/2016 | ............. A01N 63/30 |

OTHER PUBLICATIONS

K. T. Selvi et al., "Distribution of Heterocystous Cyanobacteria in Rice Fields of Cuddalore District, Tamilnadu," International Journal of Life science & Pharma Research, vol. 2, Issue 4, Oct.-Dec. 2012, pp. L-30-L-39.*

S. Nayak et al., "Soil PH and Its Role in Cyanobacterial Abundance and Diversity in Rice Field Soils," Copyright 2007, Applied Ecology and Environmental Research 5(2): 103-113.*

"Soil Quality Indicators: pH," Soil Quality Information Sheet, USDA Natural Resources Conservation Service, published Jan. 1998, pp. 1-2.*

* cited by examiner

*Primary Examiner* — Monica A Shin
(74) *Attorney, Agent, or Firm* — Hoffmann & Baron, LLP

(57) ABSTRACT

This invention refers to a bacterial inoculating formulation based on a microorganism consortium of genus *Calothrix* sp., to increase yield and quality of vegetable crops, the method for manufacturing the formulation and uses thereof, particularly its use in the industry of bacterial inoculants for field and greenhouse application, and for any other place requiring an enhancement in yield and quality of vegetable crops, without using nitrogen chemical fertilizers.

The bacterial inoculating formulation based on a microorganism consortium of genus *Calothrix* sp., to increase yield and quality of vegetable crops comprises: a) a microorganism consortium of genus *Calothrix* sp., at a concentration ranging from 0.05% to 10% by weight; b) a substrate or immobilizing vehicle in order to immobilize the microorganisms at a concentration ranging from 2% to 80% by weight; c) a soil pH buffer at a concentration ranging from 0% to 3% by weight, and d) moisture at a concentration ranging from 7% to 97.95% by weight.

12 Claims, No Drawings

BACTERIAL INOCULATING FORMULATION BASED ON A MICROORGANISM CONSORTIUM OF GENUS *CALOTHRIX* SP. TO INCREASE YIELD AND QUALITY OF VEGETABLE CROPS, THE METHOD FOR MANUFACTURING THE FORMULATION AND USES THEREOF

CROSS-REFERENCE TO RELATED APPLICATIONS

This application claims priority to Mexican Patent Application No. MX/a/2017/008876, filed on Jul. 4, 2017, the contents of which are incorporated herein by reference in its entirety.

FIELD OF THE INVENTION

This invention refers to a bacterial inoculating formulation based on a microorganism consortium of genus *Calothrix* sp., to increase yield and quality of vegetable crops, the method for manufacturing the formulation and uses thereof, particularly its use in the industry of bacterial inoculants for field and greenhouse application, and for any other place requiring an enhancement in yield and quality of vegetable crops, without using nitrogen chemical fertilizers.

More specifically, the bacterial inoculant formulation based on a microorganism consortium of genus *Calothrix* sp. promotes growth and quality of vegetable crops, which results in better yield and phenological characteristics compared with crops which did not received said formulation.

BACKGROUND OF THE INVENTION

The use of microorganism to inoculate plants and provide them with beneficial effects has been known for centuries. Based on experience, for example, farmers learned that by taking soil samples where some sort of legume had been previously grown and mixing it with other soil in which no legumes were to be grown, final yield of the different crop was frequently enhanced. For over a hundred years inoculants based on *rhizobium* bacteria have been produced all over the world, mainly by small companies. The use of inoculants has had a significant impact in countries such as U.S.A., Brazil, Argentina, Australia, Eastern Europe, Egypt, Israel, South Africa, New Zealand and to a lesser extent in Southeast Asia. However, for most of the undeveloped countries in Asia, Africa, Central and South America the use of inoculants has had no impact on crop productivity, since they are not used or they are of poor quality (Bashan, Y. 1998).

The immediate response to inoculating the soil with microorganisms promoting plant growth varies substantially depending on the microorganism, plant species, soil type, inoculant density and environment conditions. Usually, shortly after the microorganism is introduced in the soil, the population of the same progressively declines (Bashan and Levanony, 1988; van Elsas et al. 1986). This phenomenon may prevent the formation of a sufficiently abundant quantity of microorganisms to obtain the desired response in the plant. The main obstacle is that the soil is an unpredictable and heterogeneous environment, even on a small scale (van Elsas and van Overbeek, 1993). Sometimes inoculating microorganisms cannot find an empty gap in the soil to survive, except in sterilized soil, a non-existent condition in large-scale agriculture. Therefore, the must compete with native microflora, usually better adapted.

One major challenge in the formulation of inoculants is precisely to provide a more suitable microenvironment (even if only temporary) to avoid the fast decline of the microorganisms introduced in the soil (Bashan, Y. 1998). While much is known about the survival of microorganisms within de protective environment provided by an inoculant immobilizing vehicle, little is known about the stress the microorganism may suffer when transferred to a competitive-soil and frequently hostile environment (Heijnen et al. 1992; Rodriguez-Navarro et al. 1991; van Elsas y Heijnen, 1990). Thus, inoculants should be formulated to be able to provide a reliable source or beneficial microorganisms which can survive in the soil be available to the plant when said plant needs them (Bashan, Y. 1998).

It is of crucial importance to distinguish between the concepts of inoculant and biofertilizer. Inoculant refers to a formulation containing one or more strains (or species) of beneficial microorganisms in an inexpensive and easy-to-use vehicle, either organic, inorganic or synthesized from defined molecules. The inoculant is the means of conveyance of microorganisms from the factory to the living plant. The desired effects of the inoculant on plant growth include nitrogen fixation, biocontrol of diseases (mainly) characteristic of the soil, enhancement of mineral intake and erosion caused by soil minerals, as well as nutritional and hormonal effects. On the other hand, the term biofertilizer is broadly used but leads to confusion and means "bacterial inoculant". Normally, it refers to microorganism preparations which represent partial or total substitutes of chemical fertilization. However, by using the term biofertilizer other effects of the microorganisms in the plant growth are left aside (Bashan, Y. 1998).

In view of the above, it is important to consider various factors when formulating an inoculant. Firstly, the microorganism should show biological effectiveness, higher yield and protection of plants health in connection with control crops which have not been inoculated. Also, a more reliable vehicle should be pursued, at a reasonable cost so as to be of industrial interest, which keeps the microorganism dormant and allows its availability when it needs to be applied on the plant or any part thereof. Finally, it is important to add some substance which facilitates its inclusion in different types of soil in order to avoid a decline in microorganism concentration due to soil's effects (such as acidity) or due to competition effects with existent microflora in the soil.

Mexican patent MX/a/2013/007978 describes a bacterial formulation containing 6 different bacterial strains: *Azospirillum brasilense* Sp7, *Burkholderia unamae* MT1641, *Pseudomonas putida* KT2440, *Sphingomonas* sp. OF 178, *Gluconoacetobacter diazotrophicus* PAI 5 and *Bradyrhizobium* sp. MS22, capable of promoting growth in plants of agricultural and/or bioremediation interest. The formulation promotes growth in maize plants and other plants of agricultural interest. Bacteria in such document may attach themselves to and properly colonize plants by their own means, nonetheless, said document neither mentions nor suggests a bacterium of genus *Calothrix*, also it does not solve the problem of the present invention, therefore it does not affect novelty or inventive step of the present invention formulation. European patent application EP 3 090 994 A1 claims a biofertilizer based on encapsulated enzymes among which are phosphatase, arylsulphatase, asparaginase y glutaminase over an allofane substrate; organic substrates with contents of 3.08% N and 0.5% P; growth-hormone-like encapsulated organic substrates for plants such as humic and fulvic acids; and organic molecules and microorganisms beneficial for plants. U.S. Pat. No. 8,029,593 B2 claims a biofertilizer comprising bacteria of *Azopirillum brasilense* consortium together with at least one other bacterium which provides one of the following features: nitrogen fixation, lysating other bacteria in the soil, depredating and having nematicidal activity. However, none of the claimed bacteria in the patent belongs to the consortium of genus *Calothrix*. U.S. Pat. No. 8,415,271 B2 claims a biofertilizer comprising psychrophilic bacterial strains isolated from rhizosphere of plant *Deschampsia antárctica*, but the strains are from *Pseudomonas antartica, Pseudomonas trivialis* y *Anthrobacter* ssp. U.S. Pat. No. 9,187,381 B1 claims a biofertilizer and a biopesticide based on *Paenibacillus polymyxa, Azospirillum canadense* and *Bacillus pumilus*. U.S. Pat. No. 9,321,697 B2 claims a recombinant microorganism with altered genes which allows it to fix atmospheric nitrogen in the presence of fixated oxygen and nitrogen, said microorganism being *Azotobacter* spp. U.S. Pat. No. 9,499,447 B2 claims a microbial inoculant which consists of a lyophilized bacterial microorganism selected from genus *Azospirillum*. United States patent application US 2010/0300166 A1 claims a biofertilizer based on strain C-924 of the microorganism *Tsukamurella paurometabola*, which may be combined or mixed with other organic biofertilizers such as *Bacillus subtilis, Rhizobium leguminosarum, Azotobacter chroococum, Pseudomonas fluorescens, Glomus fasciculatum* and *Glomus clarum*. United States patent application US 2015/0040629 A1 claims a biofertilizer based on Mycorrhiza isolated from a crop group comprising at least one genus of air-dried fungus selected from: genus *Glomus;* genus *Gigaspora;* genus *Scutellospora*. Mexican international patent application WO03/089640 A2 claims the use of bacterium *Rhizobium* genetically modified as a biofertilizer. Korean international patent application WO03/089640 A2 claims a method to prepare a biofertilizer based on palm oil milling residues involving thermal processes. Indian international patent application WO2013/098856 A2 claims a biofertilizer formulation comprising a synergistic combination of earthworm cocoon with microorganisms such as *Azotobacter* and/or other bacteria fixing N in the presence of a biocomptaible vehicle adapted to synergistically improve soil's fertility and yield. United States international application WO2014/028698 A2 claims a biofertilizer resulting from the dry milling process of corn ethanol. Malaysian patent international application WO2014/042517 A2 claims a biofertilizer comprising at least one strain selected from the group of microorganisms *Pseudomonas aeruginosa, Serratia marcescens* and *Bacillus amyloliguefaciens*. French patent international application WO2014/163471 A1 claims a biofertilizer based on bacterium *Azospirillum*. French patent international application WO2014/163474 A1 claims a biofertilizer based on bacterium *Azotobacter*. Indian patent international application WO2015/075607 A2 claims a method for increasing nutritional and elemental content of seed using a strain of *Bacillus MCC0008* as biofertilizer. Italian patent international application WO2016/009397 A1 claims a biofertilizer based on some of the following microorganisms *Azospirillum brasilense, Gluconacetobacter diazotrophicus, Burkholderia cepacia* and *Herbaspirillum seropedicae*.

One disadvantage of the state of the art inoculants is the lack of an immobilizer at the time of application.

An additional disadvantage of current inoculants is the absence of a compound which serves as buffer when the microorganism is placed on the rhizosphere, which constitutes a problem for highly acid soils.

Yet another disadvantage of some inoculant formulation methods consists in the final form of the same, which is only limited to one state (liquid, powder, granules, emulsions, etc.).

Other disadvantage in some of the methods is the use of genetically modified microorganisms, which from the beginning cannot be classified as inoculants for organic crops, according to the United States' National Organic Program (NOP).

Some of the manufacturing methods of current inoculants employ costly culture media, which implies a disadvantage when taken to agricultural industrial scale.

Taking into account the deficiencies of the prior art, it is an object of the present invention to provide a formulation method for an inoculant based on a consortium of microorganisms of genus *Calothrix* sp., with a vehicle which allows useful viability of the same when applied to vegetable crops, and shows biological effectiveness with better yield and phenological characteristics regarding non-inoculated crops.

Another object of the present invention is to include in the formulation a substance useful as a pH buffer for those soils in which the inoculant is used. Still another object of the present invention is that the final inoculant can be sold in liquid and solid forms, the latter employing different kinds of vehicles.

Yet another object of the present invention is that the microorganisms employed to increase the crop yield are not genetically modified microorganisms.

Finally, another object of the present invention is to use a crop medium for microorganism consortium growth that is economically feasible to be used at industrial scale.

BRIEF DESCRIPTION OF THE INVENTION

This invention refers to a method to formulate an inoculant which acts as growth promoter of vegetable crops and enhancer of the phenological characteristics of the same comprising: isolating a consortium of microorganisms of genus *Calothrix* sp from the natural medium in which it is located; making it grow until an optimum concentration employing an inexpensive culture medium based on different salts, sunlight and atmospheric nitrogen; immobilizing the microorganism on an adequate support; eliminating moisture excess from the microorganism supported by a heating device not exceeding the temperature harmful for the consortium of microorganisms (50° C.); adding a substance acting as pH buffer to the supported microorganism; adapting the final form of the formulation to any of the following embodiments: solid (agglomerations, granules, powder, etc.) or liquid.

DETAILED DESCRIPTION OF THE INVENTION

This invention refers to a bacterial inoculating formulation based on a microorganism consortium of genus *Calothrix* sp., to increase yield and quality of vegetable crops, the method for manufacturing the formulation and uses thereof, particularly its use in the industry of bacterial inoculants for field and greenhouse application, and for any other place requiring an enhancement in yield and quality of vegetable crops, without using nitrogen chemical fertilizers.

More specifically, the bacterial inoculant formulation based on a microorganism consortium of genus *Calothrix* sp. promotes growth and quality of vegetable crops, which results in better yield and phenological characteristics compared with crops which did not received said formulation.

The bacterial inoculating formulation based on a consortium of microorganisms of genus *Calothrix* sp. to increase yield and quality of vegetable crops produces no phytotoxic effect on plants in any of the applied doses, therefore it can be used without risks for any crop.

The bacterial inoculating formulation based on a consortium of microorganisms of genus *Calothrix* sp. may be applied to plants in a dose of 50 up to 100 kg/ha, preferably of 61.623 kg/ha, to increase yield and quality of vegetable crops, application may be made on the rhizosphere, seeds, or plant.

In a first embodiment of the present invention, the bacterial inoculating formulation based on a consortium of microorganisms of genus *Calothrix* sp. to increase yield and quality of vegetable crops comprises:

a) A consortium of microorganisms of genus *Calothrix* sp. at a concentration ranging from 0.05% to 10% by weight;

b) a substrate o immobilizing vehicle in order to immobilize the microorganisms at a concentration ranging from 2% to 80% by weight;

c) a soil pH buffer at a concentration ranging from 0% to 3% by weight, and d) moisture at a concentration ranging from 7% to 97.95% by weight. The microorganism consortium of genus *Calothrix* sp. is selected from the group consisting of the following species: *Calothrix adscencens, Calothrix allorgei, Calothrix braunii, Calothrix castelli, Calothrix inserta, Calothrix prolifera, Calothrix thermalis,* and/or mixtures thereof.

The microorganism consortium of genus *Calothrix* sp. is preferably selected from species *Calothrix castelli.*

The species are present at a concentration ranging from: $1\times10^{1}$ to $1\times10^{30}$ UFC/g, preferably between $1\times10^{2}$ and $1\times10^{20}$ UFC/g and most preferably between $1\times10^{3}$ and $1\times10^{10}$ UFC/g.

The microorganism consortium of genus *Calothrix* sp. is in viable state (alive).

The substrate or immobilizing vehicle to immobilize the microorganisms is selected from the group consisting of leonardite mineral, polymeric material, peat, coconut ash, alginates, agar, wheat and/or corn flour, among others and/or mixtures thereof.

The polymeric material may be selected from phenol-formaldehyde resin foams for agricultural use such as ultrafoam®, peatfoam®, oasis®, agrofoam®, etc.

The soil pH buffer is selected from the group consisting of monopotassium phosphate, monosodium phosphate, calcium carbonate, bicarbonate, disodium phosphate, among others, and/or mixtures thereof.

Moisture refers to the % of water content in the formulation.

In a second embodiment of the present invention, the bacterial inoculating formulation based on a microorganism consortium of genus *Calothrix* sp. to increase yield and quality of vegetable crops comprises:

a) A microorganism consortium of genus *Calothrix* sp. is selected from the group consisting of the following species: *Calothrix adscencens, Calothrix allorgei, Calothrix braunii, Calothrix castelli, Calothrix inserta, Calothrix prolifera, Calothrix thermalis,* and/or mixtures thereof, at a concentration ranging from 0.05% to 10% by weight;

b) a substrate or immobilizing vehicle to immobilize the microorganisms is selected from the group consisting of leonardite mineral, polymeric material, peat, coconut ash, alginates, agar, wheat and/or corn, and/or mixtures thereof, at a concentration ranging from 2% to 80% by weight.

c) a soil pH buffer selected from de the group consisting of monopotassium phosphate, monosodium phosphate, calcium carbonate, bicarbonate, disodium phosphate, and/or mixtures thereof at a concentration ranging from 0% to 3% by weight, and d) moisture at a concentration ranging from 7% to 97.95% by weight.

In a third embodiment of the present invention, the bacterial inoculating formulation based on a microorganism consortium of genus *Calothrix* sp. to increase yield and quality of vegetable crops comprises:

a) A microorganism of genus *Calothrix* sp. of the species: *Calothrix castelli* at a concentration ranging from 0.05% to 10% by weight;

b) a substrate or immobilizing vehicle to immobilize the microorganisms is selected from the group consisting of leonardite mineral, polymeric material, peat, coconut ash, alginates, agar, wheat and/or corn, and/or mixtures thereof, at a concentration ranging from 2% to 80% by weight.

c) a soil pH buffer selected from de the group consisting of monopotassium phosphate, monosodium phosphate, calcium carbonate, bicarbonate, disodium phosphate, and/or mixtures thereof at a concentration ranging from 0% to 3% by weight, and d) moisture at a concentration ranging from 7% to 97.95% by weight.

In a fourth embodiment of the present invention, the bacterial inoculating formulation based on a microorganism consortium of genus *Calothrix* sp. to increase yield and quality of crop vegetables requires no pH buffer and comprises:

a) A microorganism of genus *Calothrix* sp. of the species: *Calothrix castelli* at a concentration ranging from 0.05% to 10% by weight;

b) a substrate or immobilizing vehicle to immobilize the microorganisms is selected from the group consisting of leonardite mineral, polymeric material, peat, coconut ash, alginates, agar, wheat and/or corn, and/or mixtures thereof, at a concentration ranging from 2% to 80% by weight, and c) moisture at a concentration ranging from 10% to 97.95% by weight.

In a fifth embodiment of the present invention, the formulation may be in liquid form, i.e, the microorganism consortium of genus *Calothrix* sp. is not attached to a substrate or immobilizing vehicle, it is only dispersed in water with or without the soil pH buffer, depending on the kind of soil the formulation will be applied on.

In a sixth embodiment of the present invention, the bacterial inoculating formulation based on a consortium of microorganisms of genus *Calothrix* sp. to increase yield and quality of vegetable crops comprises:

a) a consortium of microorganisms of genus *Calothrix* sp. at a concentration ranging from 0.05% to 10% by weight;

b) a soil pH buffer at a concentration ranging from 0.01% to 3% by weight, and c) moisture at a concentration ranging from 87% to 99.94% by weight.

In a seventh embodiment of the presente invention, the bacterial inoculating formulation based on a microorganism consortium of genus *Calothrix* sp. to increase yield and quality of vegetable crops comprises:

a) A consortium of microorganisms of genus *Calothrix* sp. at a concentration ranging from 0.05% to 10% by weight; and b) moisture at a concentration ranging from 90% to 99.95% by weight.

In an eighth embodiment of the present invention, the method to manufacture a bacterial inoculating formulation based on a microorganism consortium of genus *Calothrix* sp. to increase yield and quality of vegetable crops comprises the following steps:

i) Selecting a microorganism consortium of genus *Calothrix* sp. from the group consisting of the following species: *Calothrix adscencens, Calothrix allorgei, Calothrix braunii, Calothrix castelli, Calothrix inserta, Calothrix prolifera, Calothrix thermalis*, and/or mixtures thereof, at a concentration ranging from 0.05% to 10% by weight, and placing it in a container with stirrer, wherein the microorganism consortium of genus *Calothrix* sp. is in liquid form dispersed in water;

ii) Adding a substrate or immobilizing vehicle in order to immobilize the microorganisms selected from the group consisting of leonardite mineral, polymeric material, peat, coconut ash, alginates, agar, wheat and/or corn flour, and/or mixtures thereof, at a concentration ranging from 2% to 80% by weight to the container, and allowing contact for a period of time of between 1 and 50 minutes, preferably between 5 and 25 minutes and most preferably between 10 and 20 minutes, with stirring, and once this period of time has elapsed the microorganisms are attached or immobilized to the substrate or immobilizing vehicle;

iii) Removing the moisture excess from the microorganisms attached or immobilized to the substrate or immobilizing vehicle by filtration and heat exchange, during filtration microorganisms attached or immobilized to the substrate or immobilizing vehicle separate from water, the water separated containing traces of the microorganism culture medium and still containing salts, so it may be re-used to grow subsequent inoculants from the microorganisms, the filtered microorganisms attached or immobilized to the substrate or immobilizing vehicle are subsequently subjected to heat exchange, which may be performed with a heating device at a temperature no greater than 50° C., during a period of time which can range from between 1 hour and 15 hours, preferably between 2 hours and 10 hours and more preferably between 3 hours and 8 hours, until a resulting solid product is obtained, once the moisture excess is removed;

iv) mixing the resulting solid product with a soil pH buffer selected from the group consisting of monopotassium phosphate, monosodium sodium phosphate, calcium carbonate, bicarbonate, disodium phosphate and/or mixtures thereof at a concentration ranging from 0% to 3% by weight during a period of time which can range between 1 minute and 40 minutes, preferably between 5 minutes and 30 minutes and more preferably between 10 minutes and 20 minutes, until a solid product of the bacterial inoculant is obtained with a moisture content at a concentration ranging from 7% to 97.95% by weight, and v) weighing and packaging.

The heating device may be selected from tray dryer (plates) or rack dryer, indirect-heat vacuum shelf dryer, tunnel continuous dryer, rotary dryer, etc., preferably selected from the tray dryer (plates) or rack dryer through which resistor pre-heated air, or ambient air, passes, without heating in order to preserve microorganisms viability.

The formulation may be in liquid form, i.e, the microorganism consortium of genus *Calothrix* sp. is not attached to a substrate or immobilizing vehicle, it is only dispersed in water with or without the soil pH buffer, depending on the kind of soil the formulation will be applied on.

Therefore, steps ii) and iii) of the method will not be performed, i.e., no substrate or immobilizing vehicle will be added to the microorganism consortium of genus *Calothrix* sp., and moisture concentration ranges from 90% to 99.95%, by weight.

In a ninth embodiment of the present invention, the final bacterial inoculant solid product may be formulated to have, without limitation, some of the following forms: agglomerations, powder, granules, etc.

In a tenth embodiment of the present invention, the method to isolate the microorganism consortium of genus *Calothrix* sp., comprises:

a') Naturally isolating the microorganism consortium of genus *Calothrix* sp. from the soil for subsequent growing in the lab, in 1 liter flasks;

b') In order to grow, microorganisms need three elements: sunlight, nitrogen and culture medium consisting of a set of macro- and micronutrients, or salts, thereby microorganisms grow until reaching an optimum concentration ranging from 0.5 to 3.5 g/ml, preferably from 1 to 2 g/ml. Growth rate depends on sunlight availability, temperature, nitrogen, and composition used in the culture medium, as well as pH and amount of dissolved oxygen; and c') once the optimum concentration ranging from 0.5 to 3.5 g/ml, preferably from 1 to 2 g/ml, of microorganisms in a container along with the necessary requirements have been achieved, a part of them may be gaged with more culture medium so that they grow until optimum concentration in consecutive periods, thereby the microorganism consortium of genus *Calothrix* sp. may be easily taken to industrial scale for its formulation.

The culture medium is BG-11 (without nitrogen source), readily available in the literature for the skilled in the art, thus there is no need to describe it in detail. It consists of several low-cost salts, the concentrations of which were optimized to achieve a better growth rate of the microorganism consortium of genus *Calothrix* sp. (species: *Calothrix adscencens, Calothrix allorgei, Calothrix braunii, Calothrix castelli, Calothrix inserta, Calothrix prolifera, Calothrix thermalis*, and/or mixtures thereof)

EXAMPLES

The purpose of the following examples is to, without limiting, illustrate the invention, any variation thereof will be deemed as falling within the scope of the present invention.

Example 1

Manufacturing of a bacterial inoculating formulation based on a microorganism consortium of genus *Calothrix* sp. begins, following the manufacturing method of the present invention, the bacterial inoculating formulation obtained comprising: a) a microorganism consortium of genus *Calothrix* sp., at a concentration ranging from 0.05% to 10% by weight; b) a substrate or immobilizing vehicle in order to immobilize the microorganisms at a concentration ranging from 2% to 80% by weight; c) a soil pH buffer at a concentration ranging from 0% to 3% by weight, and d) moisture at a concentration ranging from 7% to 97.95% by weight.

The bacterial inoculating formulation obtained may be used to increase yield and quality of vegetable crops.

Example 2

Manufacturing of a bacterial inoculating formulation based on a microorganism consortium of genus *Calothrix* sp.

begins, following the manufacturing method of the present invention, the bacterial inoculating formulation obtained comprising: a) a microorganism consortium of genus *Calothrix* sp., at a concentration ranging from 0.05% to 10% by weight; b) a soil pH buffer at a concentration ranging from 0.01% to 3% by weight, and c) moisture at a concentration ranging from 87% to 99.94% by weight.

The formulation obtained is in liquid form, i.e., the microorganism consortium of genus *Calothrix* sp. is not attached to a substrate or immobilizing vehicle, it is only disperse in water with the soil pH buffer, depending on the kind of soil the formulation will be applied on.

The bacterial inoculating formulation obtained may be used to increase yield and quality of vegetable crops.

Example 3

Manufacturing of a bacterial inoculating formulation based on a microorganism consortium of genus *Calothrix* sp. begins, following the manufacturing method of the present invention, the bacterial inoculating formulations obtained comprising: a) a microorganism consortium of genus *Calothrix* sp., at a concentration ranging from 0.05% to 10% by weight; y b) moisture at a concentration ranging from 90% to 99.95% by weight.

The formulation obtained may be in liquid form, i.e., the microorganism consortium of genus *Calothrix* sp. is not attached to a substrate or immobilizing vehicle, it is only disperse in water without the soil pH buffer, depending on the kind of soil the formulation will be applied on.

The bacterial inoculating formulation obtained may be used to increase yield and quality of vegetable crops.

Example 4

The formulation obtained from Example 1 (F1) was tested to assess the effect on the lettuce (*Lactuca sativa* L. var. "Great lakes") crop vigor variables. During the study, the effect on vegetative development of greenhouse-grown plants was assessed, as well as the effect on yield and quality of the crop. The experiment was performed in a tunnel-type greenhouse with plastic covers. Experimental area of the study was 100 m² considering the total of the same as a useful plot. Iceberg-type lettuce seed (*Lactuca sativa* L. var. "Great lakes") was used as biological material. Seeds were seeded on 200-well polystyrene plates and were grown for 35 days. Lettuce crop was developed in black, 4 L capacity polyethylene bags. A mixture of perlite substrate:peat moss was used in a 1:1 ratio (v:v). Sowing density was 8 plants per square meter, equivalent to 80,000 plants per hectare. For irrigation application, a targeted irrigation system was used applying a dripper on a stake for each plant.

Treatments. Biological effectiveness test was performed with the formulation described in the present invention (F1). Treatments assessed were the following: 1) Absolute control (Steiner solution without N), 2) Control with commercial fertilization (complete Steiner solution (Steiner, 1961)), 3) F1 (30.812 kg/ha)+Steiner without N, 4) F1 (61.623 kg/ha)+ Steiner without N, y 5) F1 (92.435 kg/ha)+Steiner without N. Therefore, treatments 1, 3, 4 y 5 were fertilized with modified nutritional Steiner solution removing N from the same (Table 1), whereas treatment 2 was fertilized with complete Steiner solution (Table 2). 25% concentration nutritional solutions were used for all treatments.

TABLE 1

Modified Steiner solution without N.

| Salts used | g/1000 L |
|---|---|
| $MgSO_4\ 7H_2O$ | 487 |
| $K_2SO_4$ | 410 |
| $CaSO_4\ 2H_2O$ | 775 |
| $KH_2PO_4$ | 211 |
| Chelated microelements | 50 |

TABLE 2

Complete Steiner solution (Steiner, 1961).

| Salts used | g/1000 L |
|---|---|
| $Ca(NO_3)_2\ 4H_2O$ | 1060 |
| $MgSO_4\ 7H_2O$ | 487 |
| $KNO_3$ | 71 |
| $K_2SO_4$ | 347 |
| $KH_2PO_4$ | 211 |
| Chelated microelements | 50 |

All three doses used of formulation F1 were applied at three different times during development of the crop in the following manner: $1^{st}$ application at the time of transplant, applying 67.6% of the corresponding dose; $2^{nd}$ application 20 days after transplant (DAT) using 21.6% of the dosis; y $3^{rd}$ application 35 DAT using the rest of the dose (10.8%).

Application Mode. It was checked if there was a sufficient amount of moisture in the substrate, thus applications were made immediately after applying irrigation. This ensured that during inoculant application, the same was always in contact with enough moisture for the microorganism to rapidly adapt to the new environment.

For application, each dose mentioned was diluted in 32 L of water, and using a beaker an amount of 200 ml of solution was applied to each plant at the stem base, which ensured each plant had the same amount of solution applied. The same 200 ml were applied to the control treatments but of water only.

Assessed Variables. Variables related to lettuce plant vigor were the following:
Plant height (cm): measured with a flexometer from stem base to highest plant point.
Plant diameter (cm): measured with a flexometer considering head's width on the middle third of the plant.
SPAD Units: this was measured with a SPAD Minolta 502 directly on the plant leaves. Two readings were taken per plant and average was obtained.
Number of leaves: leaves forming the head of the plant were counted, without considering the first four more senescent leaves.
Days until harvesting: days from transplant until harvesting of the plants were considered.
Fresh weight yield (ton/ha): Weight on the aerial part of the plant (without contemplating the root) was considered and extrapolation to the required units was made.
Root length (cm): obtained after washing the root and measured from stem base to longest root using a flexometer.
Dry weight of root biomass (ton/ha): obtained after drying with drying furnace for 48 hours at a constant temperature of 80° C.
Dry weight of aerial biomass (ton/ha): obtained after drying with drying furnace for 72 hours at a constant temperature of 80° C.

Mineral analysis: content of N, P, K, Ca, Mg, S, Fe, Zn, Mn, Cu and B in the plant leaves was analyzed.

pH: pH was measured on green leaves, for this purpose 10 g were taken and grinded, measuring directly with a Hanna potentiometer.

Number of fungus and bacteria in the plant (leave) and soil (UFC/g): by dilution plating method.

Phytotoxicity: this variable was determined using visual scale considering damage to foliage according to Table 3.

TABLE 3

Damage level to assess phytotoxicity.

| Index | Damage percentage |
|---|---|
| 0 | No toxicity (no damage to foliage) |
| 1 | Mild toxicity (less than 10% of damage) |
| 2 | Medium toxicity (between 10 and 30% of damage) |
| 3 | Strong toxicity (between 30 and 50% of damage) |
| 4 | Very strong toxicity (greater than 50% of damage) |

Experimental Design and Statistical Analysis. For this study, a completely random design was used. Model for said design is the following:

$$Y_i = \mu + \tau_i + \varepsilon_i$$

where:
i=1, 2, . . . , n
$\mu$=Parameter, medium effect
$\tau_i$=Parameter, treatment effect
$\varepsilon_i$=Random value, observational error
$Y_i$=Observation in experimental unit Also, a comparison of averages was made by Duncan's test (p≤0.05). 20 replications per treatment were used for statistical analysis, regarding a plant as experimental unit. All plants assessed were selected randomly. For dry biomass, root length and pH 10 replications were considered; for mineral analysis three replications per treatment were considered.

Results. Based on the study performed on lettuce plants, it was observed that complete development of the crop took 85 days. Additionally, no phytotoxic effect was observed in the plants due to formulation F1 application.

Growth Variables. Results of the assessment of variables related to lettuce plant vigor are shown in Table 4. It was noted that in all cases there were significant differences between treatments (Duncan, p≤0.05). It can be seen that in variables such as height, diameter, number of leaves, yield, leave dry weight and root dry weight, control treatment without N (T0) showed the lowest values. On the other hand, in all variables the best treatment statistically was the one with complete fertilization (Steiner). It also shall be noted that medium dose of formulation F1 was statistically equal to Steiner and better than T0 in variables such as diameter, number of leaves, yield and leave dry weight. The low dose was better than T0 in diameter, number of leaves, yield and root dry weight, while the high dose was better than T0 in diameter, number of leaves, yield and leave dry weight.

Regarding root length, the best result was obtained with the high dose of formulation F1, being statistically equal to treatments T0 and Steiner. In variables such as pH y and SPAD units, the obtained results showed in both cases that the best treatments were T0 and Steiner.

Regarding yield observed in lettuce crops, results showed that medium and high doses of formulation F1 were statistically equal to Steiner treatment with complete fertilization. Particularly, medium dose was only 2.7% low than complete fertilization treatment (Steiner). Concerning height, medium dose was equal to Steiner, whereas variables such as diameter and leave dry weight all formulation F1 doses were equal to Steiner. Concerning number of leaves, the low and medium doses of formulation F1 were equal to Steiner. Regarding root length, only the high dose was equal to Steiner, and regarding root dry weight only the low dose was equal to Steiner.

TABLE 4

Variables assessed in connection with lettuce plant vigor.

| Treat. | Height (cm) | Diameter (cm) | # Leaves | Yield (Ton/ha) | Leave D.W. (Ton/ha) | Root length (cm) | Root D.W. (Ton/ha) | pH | SPAD |
|---|---|---|---|---|---|---|---|---|---|
| T0 | ‡13.15b | ‡9.29c | ‡33.6c | ‡36.3c | †2.07b | †46.3ab | †0.24c | †6.7a | ‡38.2a |
| Steiner | 15.01a | 12.06a | 41.9a | 71.5a | 3.21a | 50.7ab | 0.47a | 6.8a | 36.3a |
| LD | 13.65b | 11.28a | 41.3a | 58.0b | 2.58ab | 42.4bc | 0.37ab | 6.3ab | 31.1b |
| MD | 14.19ab | 12.02a | 40.6a | 69.7a | 3.03a | 36.8c | 0.31bc | 6.3b | 32.9b |
| HD | 13.69b | 12.09a | 37.7b | 64.5ab | 3.22a | 52.7a | 0.32bc | 6.3b | 33.9b |
| VC (%) | 14.03 | 12.85 | 11.67 | 24.49 | 24.16 | 19.85 | 32.41 | 3.09 | 14.21 |
| P | * | *** | *** | *** | ** | ** | *** | *** | *** |

Treat.: Treatment.
D.W.: Dry weight.
T0: Control without nitrogen application.
Steiner: Control with complete fertilization.
LD: 30.812 kg/ha of F1 + Steiner without N.
MD: 61.623 kg/ha of F1 + Steiner without N.
HD: 92.345 kg/ha of F1 + Steiner without N.
Each data is the average of ‡ 20 or † 10 replications. Different letters in columns denote statistical differences according with Duncan (p ≤ 0.05).
VC: Variation coefficient.
P: Probability.
ns: Not signitificant.
*, , *: Significance of <0.05, <0.01, <0.001 respectively.

This results show that, with the exception of pH y and SPAD units, all doses of formulation F1 had a positive effect in some of the variables assessed. Additionally, it was consistently observed that along with Steiner the best treatment in most of the variables was the medium dose of F1, being statistically superior to control in diameter, number of leaves, yield and leave dry weight.

Mineral Content. Results of mineral analyses are shown in Table 5. No statistical differences were found between treatments in any of the analyzed minerals regarding content of the same in lettuce leaves (Duncan, p≤0.05).

Table 6 shows as additional data the mineral uptake by aerial part of the plants. Such Table shows significant differences between treatments in the uptake of N, K, Ca, Mg, S y Cu, being consistent that T0 (fertilization without N) was the one producing lower uptake of these minerals (Duncan, p≤0.05).

Table 7 shows the results of microorganism assessment in lettuce leaves as well as the results of assessment on the soil. Said results showed no statistical differences between treatments (Duncan, p≤0.05). These results respond to a natural tendency of soil microorganisms and the phyllosphere to grow with no homogeneous densities, but forming aggregates or clusters, which hampers adequate sampling unless many replications are made.

TABLE 5

Mineral concentration in dry matter of the aerial part of lettuce plants.

| Treat. | N (%) | P (%) | K (%) | Ca (%) | Mg (%) | S (%) | Fe (ppm) | Zn (ppm) | Mn (ppm) | Cu (ppm) | B (ppm) |
|---|---|---|---|---|---|---|---|---|---|---|---|
| T0 | 2.96a | 0.39a | 4.11a | 0.58a | 0.23a | 0.22a | 97.3a | 40.1a | 65.7a | 4.46a | 30.6a |
| Steiner | 2.78a | 0.33a | 4.39a | 0.66a | 0.27a | 0.22a | 100.1a | 31.2a | 75.8a | 5.00a | 38.1a |
| LD | 3.12a | 0.27a | 5.10a | 0.81a | 0.28a | 0.22a | 130.6a | 39.5a | 84.1a | 6.09a | 39.4a |
| MD | 3.01a | 0.35a | 4.54a | 0.88a | 0.31a | 0.24a | 98.2a | 38.8a | 101.9a | 5.15a | 41.1a |
| HD | 2.96a | 0.36a | 4.39a | 0.56a | 0.22a | 0.23a | 88.9a | 36.0a | 48.4a | 5.67a | 29.8a |
| VC (%) | 15.22 | 28.72 | 12.56 | 22.32 | 18.38 | 4.72 | 27.54 | 20.07 | 39.65 | 17.47 | 22.97 |
| P | ns | ns | ns | ns | ns | ns | ns | ns | ns | ns | ns |

Treat.: Treatment.
T0: Control without nitrogen application.
Steiner: Control with complete fertilization.
LD: 30.812 kg/ha of F1 + Steiner without N.
MD: 61.623 kg/ha of F1 + Steiner without N.
HD: 92.345 kg/ha of F1 + Steiner without N.
Each data is the average of three replications. Different letters in columns denote statistical differences according with Duncan (p ≤ 0.05).
VC: Variation coefficient.
P: Probability.
ns: Not signitificant.

Particularly in the case of N and S uptake, it was noted that medium and high doses of F1 along with Steiner were the best treatments, being superior to T0. In the case of K and Cu, all doses of F1 along with Steiner were superior to T0. In terms of Ca uptake, the best treatment was F1 medium dose, whereas in terms of Mg the best treatments were the medium dose and Steiner.

The above results show that although there were no differences in mineral concentration in lettuce leaves, there were different levels of uptake by plants (Duncan, p≤0.05). Also, it shall be noted that F1 medium dose resulted in the highest mineral uptake.

TABLE 7

Leave and soil microorganism assessment of lettuce crop.

| Treat. | BACTERIA (UFC/g) Leave | Soil | FUNGUS (UFC/g) Leave | Soil |
|---|---|---|---|---|
| T0 | 4.97 X $10^7$ a | 2.07 X $10^8$ a | 9.01 X $10^6$ a | 2.40 X $10^6$ a |
| Steiner | 1.32 X $10^8$ a | 7.50 X $10^7$ a | 9.00 X $10^6$ a | 6.20 X $10^6$ a |
| LD | 5.28 X $10^7$ a | 5.60 X $10^7$ a | 3.02 X $10^7$ a | 4.73 X $10^6$ a |
| MD | 1.72 X $10^7$ a | 1.70 X $10^7$ a | 6.77 X $10^6$ a | 1.90 X $10^6$ a |
| HD | 2.72 X $10^7$ a | 2.33 X $10^7$ a | 4.87 X $10^6$ a | 3.53 X $10^6$ a |

TABLE 6

Mineral uptake by aerial part of lettuce plants (Data are shown in uptake per plant).

| Treat. | N (g) | P (g) | K (g) | Ca (g) | Mg (g) | S (g) | Fe (mg) | Zn (mg) | Mn (mg) | Cu (mg) | B (mg) |
|---|---|---|---|---|---|---|---|---|---|---|---|
| T0 | 0.77b | 0.10a | 1.06b | 0.15b | 0.06b | 0.06c | 2.52a | 1.05a | 1.70a | 0.12b | 0.79a |
| Steiner | 1.11a | 0.13a | 1.76a | 0.26ab | 0.11a | 0.09a | 4.04a | 1.27a | 3.04a | 0.20a | 1.53a |
| LD | 1.01ab | 0.09a | 1.65a | 0.26ab | 0.09ab | 0.07b | 4.22a | 1.28a | 2.72a | 0.20a | 1.27a |
| MD | 1.14a | 0.13a | 1.72a | 0.33a | 0.12a | 0.09a | 3.72a | 1.47a | 3.86a | 0.19a | 1.56a |
| HD | 1.19a | 0.15a | 1.77a | 0.22ab | 0.09ab | 0.09a | 3.58a | 1.45a | 1.94a | 0.23a | 1.20a |
| VC (%) | 13.08 | 26.74 | 13.77 | 23.77 | 19.52 | 5.14 | 25.63 | 18.79 | 40.49 | 15.14 | 24.3 |
| P | * | ns | * | * | * | *** | ns | ns | ns | ** | ns |

Treat.: Treatment.
T0: Control without nitrogen application.
Steiner: Control with complete fertilization.
LD: 30.812 kg/ha of F1 + Steiner without N.
MD: 61.623 kg/ha of F1 + Steiner without N.
HD: 92.345 kg/ha of F1 + Steiner without N.
Each data is the average of three replications. Different letters in columns denote statistical differences according with Duncan (p ≤ 0.05).
VC: Variation coefficient.
P: Probability.
ns: Not signitificant.
*, , *: Significance of <0.05, <0.01, <0.001 respectively.

TABLE 7-continued

Leave and soil microorganism assessment of lettuce crop.

| Treat. | BACTERIA (UFC/g) Leave | Soil | FUNGUS (UFC/g) Leave | Soil |
|---|---|---|---|---|
| VC (%) | 195.13 | 204.37 | 148.09 | 51.11 |
| P | ns | ns | ns | ns |

Treat.: Treatment.
T0: Control without nitrogen application.
Steiner: Control with complete fertilization.
LD: 30.812 kg/ha of F1 + Steiner without N.
MD: 61.623 kg/ha of F1 + Steiner without N.
HD: 92.345 kg/ha of F1 + Steiner without N.
UFC/g ds: Colony forming units per gram of dry soil.
Each data is the average of three replications.
Different letters in columns denote statistical differences according with Duncan (p ≤ 0.05).
VC: Variation coefficient.
P: Probability.
ns: Not signitificant.

Conclusions. Formulation F1 had no phytotoxic effect in lettuce plants in any of the assessed doses, thus it may be used with no risk for the tested crop.

Except for pH and SPAD units, all F1 doses had a positive effect on at least one of the variables tested in connection with lettuce plant vigor.

Medium and high doses of F1 together with Steiner treatment with complete fertilization produced statistically the same yield. Also, medium dose of F1 along with Steiner were the best treatments for most of the variables. All F1 doses tested were better than T0 in variables such as yield, height and number of leaves. This proves formulation F1 had a positive effect on such variables.

None of the treatments produced a higher concentration of the minerals tested in leaf tissue of lettuce plants. However, medium dose of F1 produced the highest mineral uptake of N, K, Ca, Mg, S y Cu, or was statistically equal to the highest. This suggests formulation F1 had a positive effect in mineral uptake by lettuce plants, which was reflected directly in plant growth.

The best dose of formulation F1 was the medium dose, comprising 61.623 kg/ha of product, since it generated the best results in variables such as lettuce plant vigor, as well as mineral uptake.

Example 5

The same formulation (F1) from previous example was tested on sorghum crops. Assessment was performed under drip irrigation conditions. Experimental area consisted of 1,848 m$^2$, with 5 treatments and 4 replications; each experimental plot had 6 rows of 10 m in length and a distance between rows of 0.80 m. Useful plot was 4.8 m$^2$ (2 rows of 0.8 m width by three meters long). Time between planting and harvesting was 133 days.

Treatments. In order to test biological effectiveness, the following five treatments were assessed: 1) Absolute control (AC) without fertilizer, 2) Control with chemical fertilization (CCF) N-P-K+microelements, 3) Low dose of formulation F1 (LD): 30.812 kg/ha, 4) Medium dose of formulation F1 (MD): 61.623 kg/ha and 5) High dose of formulation F1 (HD): 92.435 kg/ha.

Treatment 1 (AC) was an absolute control, where sorghum seed was placed alone without fertilizer supply. In CCF treatment, fertilization formula 198N-42P-36K-09Zn-1.4B+microelements was used, applying base fertilization with 20% nitrogen and 100% phosphorus, potassium, zinc and microelements. On the second application, 20 days post-planting (DPP) nitrogen 53% was applied and on the third application (40 days DPP) nitrogen 27% was applied (Table 7). As for the three doses used of formulation F1 (treatments 3, 4 and 5) they were applied on 3 times during crop development: 1St application when planting, applying 67.6% of total dose; 2$^{nd}$ application 20 days after planting (DAP) using 21.6% of total dose; and 3$^{rd}$ application 40 DAP using the rest of the dose (10.8% of total).

TABLE 7

Fertilization formula per hectare for *sorghum*.

| 1st fertilization | ELEMENT CONCENTRATION | | | | | | | KG OF FERTILIZER/Ha | TOTAL OF ELEMENTS |
|---|---|---|---|---|---|---|---|---|---|
| | N | P$_2$O$_3$ | K$_2$O | S | Ca | Zn | B | | |
| | | | | | | | | Application During Planting | |
| Granulated Ammonium Sulfate | 19 | | | 23.3 | 3.2 | | | 161.6 | 30.7 |
| MAP (11-52-00) | 11 | 52 | | | | | | 80.8 | 8.9N, 42P |
| Potassium Chloride | | | 60 | | | | | 60.0 | 36K |
| Zinc Sulphate | | | | | | 36 | | 25.0 | 9Zn |
| Granubor | | | | | | | 1.40% | 10.0 | |
| Microelements | 8% Fe, 6% Zn, Mg10%, Ca2% | | | | | | | 20.0 | 1.6FE, 1.2Zn, 2Mg, 0.4Ca |
| TOTAL/Ha. | | | | | | | | 357.4 | |
| | | | | | | | | Application During Development | |
| 20 DAP (2nd. fertilization), apply Ammonium Sulphate | | | | | | | | 499.5 | 104.9N |
| 40 DAP (3rd. fertilization), apply Phosphonitrate | | | | | | | | 162.0 | 53.5N |
| TOTAL/Ha. | | | | | | | | 661.5 | |

DAP: Days after planting

Assessed Variables. Assessed variables in phenological phase and quality phase are mentioned below:

Days until flowering (DF): measured when sorghum plants of each experimental plot showed 50% of panicles in medium anthesis (amount of days).

Days until physiological (DPM): days elapsed since planting until 80% of plant grains of each experimental plot changed all green coloration to red color were counted (number of days).

Plant height (PH): after flowering, 20 plants were measured from each experimental plot, recording the average distance between stem base and panicle apex (cm).

Panicle length (PL): 20 panicles in each experimental plot were quantified and average distance between panicle base apex was recorded (cm).

Panicle length (PL): 20 panicles in each experimental plot were quantified and average distance between panicle base apex was recorded (cm).

Stalk length (STK): 20 panicles in each experimental plot were quantified and average distance between flag leaf ligule and panicle base was recorded (cm).

Green residues (GR): samples were taken from 10 plants of each treatment and fresh weight of stubble was determined, without taking into account root or grain in (g).

Dried residues (DR): samples were taken from 10 plants of each treatment and dry weight of stubble was determined after furnace drying at 60° C. for 72 hrs. (g).

Harvest Index (HI): samples were taken from 10 plants of each experimental plot and percentage was determined dividing grain weight by total plant weight (without taking into account root weight) and multiplied by a hundred (%).

Stem diameter (SD): 20 plants representative of each experimental plot were selected and basal internode diameter was measured with digital vernier (mm).

Phytotoxicity (PhTx): measurement of plant and foliage damage according to the following scale (Muñoz et al, 1993), shown in Table 3

Grain yield (YLD): all plants in the useful plot for each treatment were harvested, threshed and moisture content was adjusted to 15% (ton/ha), using the methodology described by Barreto and Raun (1988). General equation for conversion is the following:

$$\text{yield ton ha}^{-1} = \left(\frac{\text{FIELD WEIGHT (kg)}}{\text{UA (m}^2\text{)}}\right) \times \left(\frac{1000 \text{ m}^2}{1 \text{ ha}}\right) \times \left(\frac{1 \text{ ha}}{1000 \text{ kg}}\right) \times MF$$

where:

$$MF \text{ (moisture conversion factor)} = \left(\frac{100 - \text{Field moisture}}{100 - \text{Adjusted moisture}}\right)$$

UA=Useful or harvested area (calculated by multiplying number or rows by row length by sowing distance between rows); 10,000=area of one hectare in m$^2$; 100=a constant based on the formula to determine humidity; Field moisture=humidity percentage measured in the field for grain weight; and moisture adjusted to 15%.

Number of grains per panicle (NGP): the total number of grains per panicle was quantified in an average of 20 panicles in each experimental plor (Number).

Weight of 1,000 grains (P1000): 1000 sorghum grains were weighed from an average of 20 planicles harvested on each experimental plot (g).

Nutritional analysis of grain (NAGr): moisture (%), carbohydrates, proteins, ashes, crude fiber and mineral (mg/g) content were determined using 200 g of a sieved sample of grains from an average of 5 panicles of each experimental plot.

Nutritional analysis of whole plant (NAWP): moisture (%), carbohydrates, proteins, ashes, crude fiber and mineral (mg/g) content were determined using 200 g of a sieved sample from an average of 5 plants on each experimental plot.

Protein percentage of grain (PPGr): protein content was determined, using a 100 g sample of grain with a moisture content of 14% by Kjeldahl method (%).

Fungus and bacteria counts in plant and soil (FunC, BacC): by dilution plating method (UFC/g).

Mineral analysis of total plant (MAP): 10 representative plants were selected from each experimental plot, they were dry to 0% moisture, grinded, and the following elements were determined: N, P, K, Ca, Mg, Fe, Zn, Cu, Mn, S and B, by Kjeldahl method (%) for N, by spectrophotometer method for P (%), S, and B (ppm), by atomic absorption method for K, Ca, Mg (%) Fe, Zn, Cu, Mn (ppm).

Experimental Design and Statistical Analysis. For this study, a completely random design was used. Model for said design is the following:

$$\gamma_{ij} = \mu | \tau_i | \beta_j | \varepsilon_{ij}$$

Where:
$\gamma_{ij}$=Response of treatment variable i of block j;
$\tau_i$=Treatment effect;
$\beta_j$=Block effect;
$\varepsilon_{ij}$=Observational error effect For average test 95% probability DMS was used ($\alpha < 0.05$).

Results. The study performed on sorghum was completed in 133 days, from planting to harvesting, after sorghum grain reached complete physiological maturity.

It is important to note that treatments 3 (Low dose), 4 (Medium dose) and 5 (High dose), which used formulation F1 in sorghum crops, were not added any other mineral element, i.e., they did not receive any other source of N, P, K, Ca, Mg, S, Fe, Zn or microelements, and together with treatment 1 (Absolute control) they did not receive chemical nitrogen.

Assessed variables in phenological phase from growth to maturity. In the results of variables related to the phenological phase, it was observed that Days until flowering (DF) results were highly significant, with a low variation coefficient (VC) of 3.405%, showing treatment 2, control with chemical fertilization (CCF), was the earliest with 55.5 days, followed by treatment 3, Low dose (LD), with 61.5 days, showing that latest treatment was treatment 1, "Absolute control" (AC),with 63.5 days, with differences of 8 and 2 two days of delay when compared to treatments CCF and LD, respectively. This indicates there is biological effectiveness in all three doses applied of formulation F1 when compared with absolute control, since days until flowering decreased (Table 8).

Results of variable Days until physiological maturity (DPM) were also highly significant with a VC under 3.047%, showing treatment 1 (AC) had the longest time till physiological maturity with 92.5 days versus 85.5, 83.25 and 77 days till physiological maturity of treatments MD, LD and CCF respectively, which in practical terms means a difference of more than eight days when it is convenient to hasten grain drying and harvesting. In this study, treatment assessed have the same tendency in physiological maturity with days to flowering of sorghum crop, thus all three doses of formulation F1 possess biological effectiveness when compared to treatment 1 or Absolute control (Table 8).

For plant height (PH) and panicle length (PL) results were very significant with a VC of 5.005% and 5.191% respectively. Treatment with highest height and longest panicle was CCF with 137.1 and 24.625 cm, while the lowest PH and PL was obtained with HD with 119.2, 21.2 cm respectively. The other treatments of interest in the study, DM and DB, showed statistical parity to treatment 1 (AC); although statistically they are on the same "b" group, treatment 1 (AC) against LD, MD and HD, differences in cm add a slight gain through crop production cycle, which means greater yield for the treatments in the study (LD, MD and HD). For stalk length (STK) results were statistically not significant (ns), yet two groups were formed in which treatment 1 (AC) had the highest STK, with 38.625 cm and from the same statistical group "a", MD, HD and LW with 38.3, 37.225 and 35.825 cm respectively, while CCF had the lowest STK with 33.725 cm in the statistical group "b", which also contained LD and MD.

For variables such as Green residues (GR), Dry residues (DR) and Harvest index (HI) results were similar regarding metabolic effectiveness, being CCF treatment the one with highest values with 229.75 and 89.25 g of GR and DR respectively, and also 15. 8% of HI and forming statistical group "a". Although treatment 1 (AC) showed the lowest values in GR, DR and HI with 143 and 55.5 g respectively and 9.9% of HI, treatments MD and LD had numerical superiority to treatment 1 (AC) with 178.5 and 159.75 g of GR respectively, and 66.25, 61.5 g of DR, respectively, and HI with 11.5, 10.68 and 10.25 respectively (Table 8). Variables GR and DR were statistically very significant and variable HI was statistically highly different. Treatments in which all three doses of formulation F1 were applied showed greater weight of GR and DR and greater percentage in HI when compared to treatment 1 (AC), which suggests formulation F1 has biological effectiveness.

Stem diameter (SD) showed very significant statistical differences, forming two groups in which group "a" was only formed by CCF treatment with 11.288 mm, 1.225 mm more than treatment 1 (AC) with 10.063 mm. Treatments LD, MD were within the same statistical group as treatment 1 (AC) with 10.398 and 10.205 mm respectively, and numerical superiority in relation to treatment 1 (AC) of 0.335 and 0.142 mm, the same results which add superiority to the final result that was harvesting (Table 8).

No phytotoxicity variable (PhTx) was observed in any treatment during development and maturity of sorghum plants according to damage measured in plants and foliage according to the scale in Muñoz et al, (1993).

TABLE 8

Averages of assessed treatments in a growth to maturity ratio of *sorghum* treatments.

| Treat. | DF (d) | DPM (d) | PH (cm) | PL (cm) | STK (cm) | GR (g) | DR (g) | HI (%) | SD (mm) |
|---|---|---|---|---|---|---|---|---|---|
| 2 CCF | 55.50b | 77.00d | 137.10a | 24.62a | 33.73b | 229.75a | 89.25a | 15.80a | 11.28a |
| 3 LD | 61.50a | 83.25c | 119.77b | 22.35b | 35.83ab | 159.75b | 61.50b | 10.68b | 10.39b |
| 4 MD | 62.50a | 85.50cb | 119.70b | 21.75b | 38.30a | 178.50b | 66.25b | 11.55b | 10.21b |
| 5 HD | 63.25a | 87.50b | 119.20b | 21.20b | 37.23ab | 152.75b | 59.75b | 10.25b | 9.97b |
| 1 AC | 63.50a | 92.50a | 124.93b | 22.23b | 38.63a | 143.00b | 55.50b | 9.90b | 10.06b |
| DMS(05) | 3.2133 | 3.9978 | 9.5724 | 1.7941 | 3.616 | 45.674 | 16.753 | 2.4121 | 0.65 |
| P | *** | *** | ** | ** | ns | ** | ** | *** | ** |
| VC (%) | 3.405 | 3.047 | 5.005 | 5.191 | 6.388 | 17.16 | 16.36 | 13.46 | 4.068 |

Treat. = Treatment;
AC = absolute control;
CCF = commercial control (198-42-36) + micros);
LD = low dose (F1 30.81 kg/ha);
MD = medium dose (F1 61.62 kg/ha);
HD = high dose (F1 92.43 kg/ha);
DF = days until flowering;
DPM = days until physiological maturity;
PH = plant height;
PL = panicle length;
STK = panicle stalk;
GR = Green residue;
DR = Dry residue;
HI = Harvest Index;
SD = Stem diameter in milimeters (mm).
The different letters in columns indicate statistical differences according to DMS (p ≤ 1.05);
P = Probability;
ns = not significant;
* (significant),  (very significant), * (highly significant) of the significance of <0.05, <0.01, <0.001 respectively;
VC = Variation coefficient;
d = days;
cm = centimeters;
g = grams;
% = percentage;
mm = milimeters.

Assessed variables in the quality phase. Among the variables studied in the quality phase, the Grain yield (YLD) variable was the most important one due to its nature of final product, which is demanded and paid for in the market.

Grain yield (YLD) variable showed highly significant statistical results, forming three groups. In the first statistical group "a" was treatment 2 (CCF), which exhibited the highest value with 3.772 ton/ha, in other statistical groups "b" and "bc" were treatment 3 (LD) with 2.031 ton/ha, treatment 4 (MD) with 1.886 ton/ha, and treatment 5 (DA) with 1.545 ton/ha; finally in group "c" was treatment 1 (AC) with 1.294 ton/ha, which had the lowest yield. The VC had a value of 20.19%, which denotes that the data obtained are reliable. Results clearly show there is a favorable effect in Grain yield per hectare in all three doses of formulation F1 (low, medium and high) over absolute control.

The results of variables Number of grains per plant (NGP) and Weight of 1,000 grains (P1000) had highly significant and significant statistical differences, respectively with a VC of 30.45% and 4.64% respectively. Treatment 1 (AC) showed the lowest values with 231.95 grains per panicle and 28.95 g by weight of 1000 grains. Treatments 3 (LD), treatment 4 (MD) and treatment 5 (HD) showed greater values in both variables when compared to treatment 1 or absolute control (AC). These two variables constitute yield, therefore their behavior in treatments follows the same tendency as Grain yield, thus biological effectiveness of formulation F1 is apparent (Table 9).

TABLE 9

Averages of assessed treatments in a quality ratio of *sorghum* treatments.

| Treat. | YLD (ton/ha) | NGP (No.) | P1000 (No.) |
|---|---|---|---|
| 2 CCF | 3.7721 a | 592.85a | 32.325a |
| 3 LD | 2.0313b | 269.60b | 28.950b |
| 4 MD | 1.886bc | 335.20b | 31.025ab |
| 5 HD | 1.545bc | 247.20b | 30.825ab |
| 1 AC | 1.2943c | 231.95b | 29.775b |
| DMS(05) | 655.23 | 157.33 | 2.187 |

TABLE 9-continued

Averages of assessed treatments in a quality ratio of *sorghum* treatments.

| Treat. | YLD (ton/ha) | NGP (No.) | P1000 (No.) |
|---|---|---|---|
| P | *** | *** | * |
| VC (%) | 20.193 | 30.45 | 4.64 |

Treat. = Treatment.
AC = absolute control;
CCF = commercial control (198-42-36) + micros);
LD = low dose (F1 30.81 kg/ha);
MD = medium dose (F1 61.62 kg/ha);
HD = high dose (F1 92.43 kg/ha);
YLD = yield;
NGP = number of grains per panicle;
P1000 = weight of a thousand grains.
The different letters in columns indicate statistical differences according to DMS ($p \leq 1.05$);
P = Probability;
ns = not significant;
* (significant),
** (very significant),
*** (highly significant) of the significance of <0.05, <0.01, <0.001 respectively;
VC = Variation coefficient.

Nutritional Analysis Of The Plant. Nutritional analysis of grain and whole plant showed not-significant results for the five treatments in variables such as moisture and volatile matter, protein in plant, ether extract, dry matter, crude fiber, nitrogen-free extract and ashes. Treatment 4 (MD), treatment 5 (HD) and treatment 3 (LD) showed greater values in variables such as moisture and volatile matter (MVM), protein in plant (PP), ether extract (EE), crude fiber (CF) and ashes (A) qhen compared to treatment 1 or absolute control (AC), which makes obvious the biological effectiveness of formulation F1 (Table 10).

Variable Protein percentage of grain (PPG) showed very significant results and a low variation coefficient (VC) of 11.97%, treatment 2 or control with chemical fertilization (CCF) showed the highest percentage of protein with 8.7% and treatments 5 (HD) and treatment 4 (MD) showed numerical superiority with 7.17% and 6.77%, greater than absolute treatment (AT) with 6.75%, which again proves the biological effectiveness of formulation F1 (Table 10) on sorghum crops.

TABLE 10

Averages of treatments assessed in connection with quality of *sorghum* treatments from nutritional analysis of grain and whole plant, and also grain protein.

| Treat. | MVM % | PP % | EE % | DM % | CF % | NFE % | A % | PPG % |
|---|---|---|---|---|---|---|---|---|
| 1 AC | 6.7300a | 12.5175b | 11.0700b | 93.2700a | 26.6500ab | 54.295a | 8.7625a | 6.7525b |
| 2 CCF | 6.8625a | 23.2325a | 21.5150a | 93.1375a | 27.6050ab | 51.990ab | 8.7950a | 8.7075a |
| 3 LD | 6.9350a | 32.7450ab | 31.1275ab | 93.0650a | 25.9580b | 54.188a | 9.0475a | 6.5550b |
| 4 MD | 6.6200a | 42.8675ab | 41.4475ab | 93.3800a | 29.7350a | 49.665b | 9.6650a | 6.7725b |
| 5 HD | 6.9100a | 52.8125ab | 51.3775ab | 93.0900a | 27.7300ab | 52.038ab | 9.1800a | 7.1725b |
| DMS(05) | 0.5236 | 0.6107 | 0.4329 | 0.5236 | 3.7403 | 4.5163 | 1.4347 | 1.3269 |

TABLE 10-continued

Averages of treatments assessed in connection with quality of *sorghum* treatments from nutritional analysis of grain and whole plant, and also grain protein.

| Treat. | MVM % | PP % | EE % | DM % | CF % | NFE % | A % | PPG % |
|---|---|---|---|---|---|---|---|---|
| P | ns | ns | ns | ns | ns | ns | ns | ** |
| VC (%) | 4.989 | 13.98 | 21.488 | 0.364 | 8.816 | 5.59 | 10.244 | 11.97 |

Treat. = Treatment.
AC = absolute control;
CCF = commercial control (198-42-36) + micros);
LD = low dose (F1 30.81 kg/ha);
MD = medium dose (F1 61.62 kg/ha);
HD = high dose (F1 92.43 kg/ha);
.HMV = moisture and volatile matter, (method: AOAC* 930.36);
PP = Plant protein (% N × 6.25) (method: AOAC 954.04);
EE = ether extract (method: AOAC 954.02);
DM = Dry matter (method: By difference);
CF = crude fiber (method AOAC 930.36);
NFE = nitrogen-free extract (method: By difference);
A = ashes (method AOAC 942.05);
PPG = protein percentage of grain (Protein (% N × 6.25))(method AOAC 954.04).
The different letters in columns indicate statistical differences according to DMS (p ≤ 0.05););
P = Probability;
ns = not signiticant;
* (significant),  (very significant), * (highly significant) of the significante of <0.05, <0.01, <0.001 respectively;
VC = Variation coefficient;
AOAC* = Official Methods of Analysis of the Association of Official Analytical Chemists.

Mineral Content. Results of minerals N, P, K, Ca, Mg, S, Fe, Zn, Mn, Cu and B in leaves and stems of plants in this study are shown below (Table 11).

Microorganisms In Soil and Plant. Table 12 shows the results of the microorganisms assessment in sorghum crop leaves, as well as assessment in soil.

TABLE 11

Average of 4 replications of treatments assessed in connection with the presence of elements such as Nitrogen (N), Phosphorus (P), Potassium (K), Calcium (Ca) and Magnesium (Mg) in treated *sorghum* plants in this study.

| Treat. | N (%) | P (%) | K (%) | Ca (%) | Mg (%) | Zn (ppm) | Cu (ppm) | Fe (ppm) | Mn (ppm) | S (ppm) | B (ppm) |
|---|---|---|---|---|---|---|---|---|---|---|---|
| 1 AC | 0.9558b | 0.869a | 1.205abc | 0.4405a | 0.256a | 0.00a | 540.29a | 663.4a | 1873.6a | 17.065a | 0.001a |
| 2 CCF | 1.3013a | 0.506a | 1.6865a | 0.4728a | 0.210ab | 0.00a | 528.86a | 965.0a | 2053.1a | 19.391a | 1.895a |
| 3 LD | 1.0468ab | 0.751a | 1.3663ab | 0.4150a | 0.247ab | 0.00a | 522.11a | 1048.1a | 1947.8a | 16.095a | 0.001a |
| 4 MD | 1.0248ab | 4.186a | 1.1620bc | 0.4785a | 0.280a | 0.00a | 561.26a | 564.9a | 2204.0a | 17.044a | 0.001a |
| 5 HD | 0.8828b | 1.037a | 0.8253c | 0.6095a | 0.155b | 86.47a | 423.51b | 604.5a | 1747.4a | 26.804a | 0.001a |
| DMS (05) | 0.3227 | 4.6413 | 0.5019 | 0.398 | 0.094 | 119.16 | 97.211 | 1474.6 | 607.5 | 13.615 | 2.6096 |
| P | ns | ns | * | ns | Ns | ns | ns | ns | ns | ns | ns |
| VC (%) | 20.098 | 204.97 | 26.0816 | 53.491 | 26.631 | 447.187 | 12.246 | 124.439 | 20.065 | 45.838 | 446.035 |

Treat. = Treatment.
AC = absolute control;
CCF = commercial control (198-42-36) + micros);
LD = low dose (F1 30.81 kg/ha);
MD = medium dose (F1 61.62 kg/ha);
HD = high dose (F1 92.43 kg/ha);
nitrogen = N;
phosphorus = P;
potassium = K;
calcium = Ca and
magnesium = Mg);
all in percentage. The different letters in columns indicate statistical differences according to DMS (p ≤ 0.05);
P = Probability;
ns = not significant;
* (significant),  (very significant), * (highly significant) of the significance of <0.05, <0.01, <0.001 respectively;
VC = Variation coefficient.

TABLE 12

Assessment of microorganisms in leave and soil of sorghum crop, averages of *sorghum* assessed treatments.

| Treat. | FC (UFC/g ds) plant | soil | BC (UFC/g ds) plant | soil |
|---|---|---|---|---|
| 1 AC | $3.00 \times 10^6$a | $7.67 \times 10^6$b | $4.88 \times 10^8$a | $3.11 \times 10^8$a |
| 2 CCF | $1.65 \times 10^7$a | $1.96 \times 10^7$a | $7.06 \times 10^6$a | $5.13 \times 10^7$a |
| 3 LD | $3.13 \times 10^6$a | $5.67 \times 10^6$b | $7.05 \times 10^6$a | $4.63 \times 10^7$a |
| 4 MD | $3.73 \times 10^6$a | $8.67 \times 10^6$b | $4.93 \times 10^6$a | $7.00 \times 10^7$a |
| 5 HD | $0.88 \times 10^6$a | $7.67 \times 10^6$b | $1.43 \times 10^6$a | $1.13 \times 10^7$a |
| DMS(05) | $1.94 \times 10^7$ | $0.835 \times 10^6$ | $7.07 \times 10^8$ | $4.42 \times 10^8$ |
| P | ns | * | ns | ns |
| VC (%) | 189.06 | 44.984 | 368.41 | 304.43 |

Treat. = Treatment.
AC = absolute control;
CCF = commercial control (198-42-36) + micros);
LD = low dose (F1 30.81 kg/ha);
MD = medium dose (F1 61.62 kg/ha);
HD = high dose (F1 92.43 kg/ha);
FunC = fungus count in plant and soil;
BacC = bacteria count in plant and soil;
UFC/g ds = colony forming units per gram of dry soil.
The different letters in columns indicate statistical differences according to DMS (p ≤ 1.05);
P = Probability;
ns = not significant;
* (significant),
** (very significant),
*** (highly significant) of the significance of <0.05, <0.01, <0.001 respectively;
VC = Variation coefficient.

Conclusions. None of the treatments produced any phytotoxic effect on sorghum plants at any dose assessed, thus formulation F1, at any dose, may be used with no risk for the crop tested.

All doses of formulation F1 had a positive effect on the variables tested regarding sorghum plant vigor.

Treatment 2, or complete chemical fertilization (CCF), treatment 3, or low dose (LD), treatment 4, or medium dose (MD), and treatment 5, or high dose (HD), of formulation F1 expressed greater sorghum grain yield, all of them outperforming absolute control, which suggests the three doses of formulation F1 have biological effectiveness on sorghum crops. Additionally, LD and MD treatments of formulation F1, together with CCF treatment, were the best treatments for most variables.

None of the treatments produced a higher concentration of the minerals tested in leaf tissue of sorghum plants. However, medium dose of formulation F1 produced the highest mineral uptake of N, K, Ca, Mg, S and Cu.

No statistical differences were found in the number of microorganisms (fungus or bacteria) in sorghum plant or soil.

The best doses of formulation F1 were the low dose (LD) and the medium dose (MD) which had 61.623 kg/ha, since they produced the best results for the sorghum plant vigor variable.

Example 6

With the formulation obtained in Example 1 and/or liquid formulation, application may proceed to the following crop families selected from: Solanaceae, Cucurbitaceae, Alliaceae, Amaryllidaceae, Apiaceae, Brassicaceae, Chenopodiaceae, Asteraceae, Liliaceae, Umbelliferae, Colvolvulaceae, Fabaceae, Poaceae, Pedialiaceae, ornamentals, and tree nurseries, among others, etc.

Example 7

This example shows a way to isolate the microorganism consortium *Calothrix* sp from the natural environment where it is located. Biological material from which microorganisms of interest are isolated is constituted by microorganisms present in a natural source, such as water bodies on fields in certain areas of the country. Firstly, it was sought that such bodies were formed by characteristic photosynthetic microorganisms of green-blue coloration. Once water bodies with such characteristics were identified, samples were taken and modified BG11 culture medium was added, removing the nitrogen source, and they were exposed to a light source to continue photosynthesis process.

Between 72 and 96 h after sampling, biofilms begun to form, which were isolated, and it was confirmed by microscope if they were filamentous microorganisms. To the isolated biofilms was again added BG11 culture medium—without nitrogen source—and they were aired; growth of microorganisms allowed the accumulation of biomass, which was purified by removing other forms of life which were of no interest, such as rotifers and various bacteria.

Once sufficient biomass of microorganisms belonging to consortium *Calothrix* sp. was accumulated, it was placed on a Petri dish and a solid culture was made exposed to light (~13.5 μmol/m²-s) at a temperature between 30-32° C. and it was incubated for 96 to 120 h. From this culture, once again a microorganism sample was isolated containing heterocytes, in order to select the purest cells possible, creating an axenic culture. Said culture was isolated and transferred to another container for its replication, using light sources, air, and modified BG11 medium. In order to preserve the strain, it was lyophilized under standard conditions in the art and the powder was preserved under controlled conditions (4° C., <40% moisture).

Finally, solid cultures were continually made on Petri dishes and preserved at 4° C. in order to have a fresh strain ready to inoculate greater-scale containers.

Example 8

Final formulation obtained in Example 1 was used in order to obtain a granular form of the product. For that purpose, a rotary plate granulator was used tilted 20° from vertical and a rotation rate between 500 and 4500 rpms, and preferably between 3000 and 3500 rpms. Product was added to granulator, along with a binder and water. Binder was added in a 0.15:1.00 ratio to total weight of final product, while water was sprayed continually until moisture content of final product increased from 6 to 8%, before passing through a tunnel dryer in which basically all water sprayed during granulate was removed. Calcium sulfate was used as binder.

Although a specific form of embodiment of the present invention was shown and described in detail by way of example, it should be understood that the present invention may be subject to various modifications and alternative forms, without departing from the spirit and scope of the present invention. Therefore, it is not intended to limit the invention to any particular form described, but instead to cover all modifications, equivalents and alternatives falling within the scope of the invention as claimed in the appended claims.

The invention claimed is:

1. A bacterial inoculating formulation based on a microorganism consortium of genus *Calothrix* sp. to increase yield and quality of vegetable crops, consisting of:

a) a consortium of microorganisms of genus *Calothrix* sp. at a concentration ranging from 0.05% to 10% by weight, wherein the consortium of microorganisms of genus *Calothrix* sp. are selected from the group consisting of the following species: *Calothrix adscencens, Calothrix allorgei, Calothrix braunii, Calothrix castelli, Calothrix inserta, Calothrix prolifera, Calothrix thermalis*, and mixtures thereof, wherein the consortium of microorganisms of genus *Calothrix* sp. are present at a concentration ranging from $1 \times 10^1$ to $1 \times 10^{30}$ CFU/g;

b) a substrate or immobilizing vehicle to immobilize the microorganisms at a concentration ranging from 2% to 80% by weight, wherein the substrate or immobilizing vehicle to immobilize the microorganisms is selected from the group consisting of leonardite mineral, phenol-formaldehyde resin foams for agricultural use, coconut ash, agar, and mixtures thereof;

c) a soil pH buffer at a concentration ranging from 0.01% to 3% by weight, wherein the soil pH buffer is selected from the group consisting of monopotassium phosphate, monosodium phosphate, disodium phosphate, and mixtures thereof; and d) water at a concentration ranging from 7% to 97.95% by weight.

2. The formulation according to claim 1, wherein the consortium of microorganism of genus *Calothrix* sp. is a *Calothrix castelli* species.

3. The formulation according to claim 1, wherein the consortium of microorganisms of *Calothrix* sp. are present at a concentration ranging from $1 \times 10^2$ and $1 \times 10^{20}$ UFC/g.

4. The formulation according to claim 1, wherein the consortium of microorganisms of genus *Calothrix* sp. are in viable state (alive).

5. The formulation according to claim 1, wherein the formulation is in the form selected from the group consisting of agglomerations, powder, and granules.

6. The formulation according to claim 3, wherein the consortium of microorganisms of genus *Calothrix* sp. are present at a concentration ranging from $1 \times 10^3$ and $1 \times 10^{10}$ CFU/g.

7. A method for manufacturing the bacterial inoculating formulation of claim 1, the method comprising:

naturally isolating a microorganism consortium of genus *Calothrix* sp. from soil;

growing the microorganisms in a culture medium until reaching a concentration ranging from 0.5 to 3.5 g/ml;

selecting a consortium of microorganisms of genus *Calothrix* sp. from the group consisting of the following species: *Calothrix adscencens, Calothrix allorgei, Calothrix braunii, Calothrix castelli, Calothrix inserta, Calothrix prolifera, Calothrix thermalis*, and mixtures thereof, at a concentration ranging from 0.05% to 10% by weight, and placing it in a container with stirrer, wherein the consortium of microorganisms of genus *Calothrix* sp. is in liquid form dispersed in water;

adding a substrate or immobilizing vehicle selected from the group consisting of leonardite mineral, phenol-formaldehyde resin foams for agricultural use, coconut ash, agar, and mixtures thereof, at a concentration ranging from 2% to 80% by weight to the container, and allowing contact for a period of time of between 1 and 50 minutes with stirring, and once this period of time has elapsed the microorganisms are attached or immobilized to the substrate or immobilizing vehicle;

removing excess moisture from the microorganisms attached or immobilized to the substrate or immobilizing vehicle by filtration and heat exchange, wherein during filtration microorganisms attached or immobilized to the substrate or immobilizing vehicle separate from water, and the filtered microorganisms attached or immobilized to the substrate or immobilizing vehicle are subsequently subjected to heat exchange at a temperature no greater than 50° C., during a period of time ranging between 1 hour and 15 hours, until a resulting solid product is obtained; and mixing the resulting solid product with a soil pH buffer selected from the group consisting of monopotassium phosphate, monosodium phosphate, disodium phosphate and mixtures thereof at a concentration ranging from 0.01% to 3% by weight for a period of time ranging between 1 minute and 40 minutes, until a solid product of the bacterial inoculant is obtained with a moisture content at a concentration ranging from 7% to 97.95% by weight.

8. The method according to claim 7, wherein the heat exchange is performed with a heating device selected from the group consisting of tray dryer, rack dryer, indirect-heat vacuum shelf dryer, tunnel continuous dryer, and rotary dryer.

9. The method according to claim 8, wherein the heating device is a tray dryer or rack dryer through which resistor pre-heated air or ambient air passes without heating in order to preserve microorganisms viability.

10. A method of increasing yields and quality of vegetable crops, comprising:

utilizing the bacterial inoculating formulation of claim 1, to increase yield and quality of vegetable crops without producing phytotoxic effect in plants.

11. The method according to claim 10, wherein the bacterial inoculating formulation is applied at a dose from 50 to 100 kg/ha where application is made to the rhizosphere, seeds or the plant.

12. The method according to claim 10, wherein the bacterial inoculating formulation is applied to crop families selected from the group consisting of *Solanaceae, Cucurbitaceae, Alliaceae, Amaryllidaceae, Apiaceae, Brassicaceae, Chenopodiaceae, Asteraceae, Liliaceae, Umbelliferae, Colvolvulaceae, Fabaceae, Poaceae*, and *Pedialiaceae*.

* * * * *